US011796787B2

(12) United States Patent
Jiang

(10) Patent No.: US 11,796,787 B2
(45) Date of Patent: Oct. 24, 2023

(54) SAMPLE IMAGE CAPTURING SYSTEM AND METHOD, AND COMPUTER-READABLE STORAGE MEDIUM

(71) Applicant: SHENZHEN MINDRAY BIO-MEDICAL ELECTRONICS CO., LTD., Shenzhen (CN)

(72) Inventor: Bin Jiang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

(21) Appl. No.: 17/585,061

(22) Filed: Jan. 26, 2022

(65) Prior Publication Data
US 2022/0244518 A1 Aug. 4, 2022

(30) Foreign Application Priority Data

Feb. 4, 2021 (CN) .......................... 202110154970.7

(51) Int. Cl.
G02B 21/36 (2006.01)
G02B 21/26 (2006.01)
G01N 33/50 (2006.01)
G01N 33/86 (2006.01)
H04N 23/61 (2023.01)
H04N 23/667 (2023.01)
G01N 15/10 (2006.01)
G01N 15/00 (2006.01)

(52) U.S. Cl.
CPC ....... *G02B 21/365* (2013.01); *G01N 33/5002* (2013.01); *G01N 33/86* (2013.01); *G02B 21/26* (2013.01); *H04N 23/61* (2023.01); *H04N 23/667* (2023.01); *G01N 2015/008* (2013.01); *G01N 2015/1006* (2013.01)

(58) Field of Classification Search
None
See application file for complete search history.

(56) References Cited

U.S. PATENT DOCUMENTS

2014/0104292 A1\* 4/2014 Radostitz ............... H04N 23/11
345/589
2020/0387742 A1\* 12/2020 Steenhoek ........... G06V 10/757
2021/0129134 A1\* 5/2021 Campton ................ B01L 3/508

\* cited by examiner

*Primary Examiner* — Eileen M Adams
(74) *Attorney, Agent, or Firm* — Kory D. Christensen

(57) ABSTRACT

A sample image capturing system includes a sample holding apparatus configured to hold a sample slide on which a sample film is applied; an imaging apparatus configured to capture the sample on the sample slide; a sample appearance image obtaining apparatus configured to obtain a sample appearance image, where the sample appearance image includes at least an appearance image of the sample film; and a controller configured to: obtain the sample appearance image, identify an appearance characteristic of the sample film based on the sample appearance image, determine a capturing parameter based on the appearance characteristic, and control the imaging apparatus to capture, with the capturing parameter, sample components on the sample slide. The disclosure further relates to a sample image capturing method and a computer-readable storage medium. The disclosure can use a characteristic of the appearance image to achieve accurate capturing of sample images.

19 Claims, 9 Drawing Sheets

SAMPLE IMAGE CAPTURING SYSTEM AND METHOD, AND COMPUTER-READABLE STORAGE MEDIUM

CROSS-REFERENCE TO RELATED APPLICATIONS

This application claims the benefit of priority to Chinese Patent Application No. 202110154970.7, entitled "SAMPLE IMAGE CAPTURING SYSTEM AND METHOD, AND COMPUTER-READABLE STORAGE MEDIUM" and filed on Feb. 4, 2021, the contents of which are incorporated herein by reference.

TECHNICAL FIELD

The disclosure relates to the sample image capturing field, and in particular, to a sample image capturing system, a sample image capturing method, and a computer-readable storage medium.

BACKGROUND

A cell morphology analyzer (also referred to as a digital microscope) is an instrument used to analyze cells on slides or smears carrying peripheral blood, bone marrow, body fluids, etc. The cell morphology analyzer includes a microscopic optical module and a digital capturing module. A main working principle of the cell morphology analyzer is as follows: An intelligent image processing algorithm is applied to automatically recognize a monolayer cell region, and blood cells (white blood cells, red blood cells, platelets, etc.) in the monolayer cell region are searched and captured; after necessary image processing is performed on captured cell images, types and characteristics of the captured cells are identified by using an intelligent recognition algorithm; and then, the captured cell images are classified and presented on a display based on the characteristics of the cells. Thus, a user, e.g., a physician, can adjust the classification result of the instrument based on clinical experience and relevant information of the patient, and give a corresponding clinical diagnosis.

Existing cell morphology analyzers only focus on local regions or single cells on a smear, and do not pay attention to the form of an entire sample film (a film, such as a blood film, formed after a sample is applied to a slide) on the smear, ignoring information about a global appearance of the sample film. For example, current cell morphology analyzers obtain a magnified microscopic image of a blood cell, and a user can only view a sharp image of a local region or a single cell, without knowing the captured region and the position of the cell on the blood film. However, the blood cell images captured in different positions on the blood film are usually of great clinical value to users.

In addition, existing cell morphology analyzers usually use a uniform capturing mode or capturing parameter to capture images of samples on sample slides of the same type. However, not all of the sample slides are very standard, that is, sample films on the sample slides vary in form, for example, some of which are long while some are short. As a result, appropriate or desired capturing positions on the sample slides are different. If a uniform capturing mode or capturing parameter is used for capturing, it is possible that no appropriate or desired sample image, or even no sample image, can be captured.

SUMMARY

Therefore, an object of the disclosure is to provide a technical solution that can fully utilize appearance and form information of a sample film on a sample slide. The technical solution can obtain an appearance image of the entire sample slide, especially an appearance image of the entire sample film on the sample slide, and use information carried in the appearance image to guide a cell morphology analyzer to capture images of cells, which can not only improve automation and intelligence of the cell morphology analyzer, but can also implement accurate sample image capturing.

To realize the object, a first aspect of the disclosure provides a sample image capturing system, including:

a sample holding apparatus configured to hold a sample slide to be tested on which a sample film to be tested is applied;

an imaging apparatus configured to capture images of the sample on the sample slide to be tested that is held by the sample holding apparatus;

a sample appearance image obtaining apparatus configured to obtain a sample appearance image of a side of the sample slide to be tested, on which side the sample film to be tested is applied, where the sample appearance image includes at least an appearance image of the sample film; and a controller communicatively connected to the imaging apparatus and the sample appearance image obtaining apparatus and configured to: obtain the sample appearance image from the sample appearance image obtaining apparatus, identify an appearance characteristic of the sample film based on the sample appearance image, determine a capturing parameter based on the appearance characteristic, and control the imaging apparatus to capture, with the capturing parameter, images of sample components in the sample film on the sample slide to be tested.

A second aspect of the disclosure provides a sample image capturing system, where the sample image capturing system includes:

a sample holding apparatus configured to hold a sample slide to be tested on which a sample film to be tested is applied;

an imaging apparatus configured to capture images of the sample on the sample slide to be tested that is held by the sample holding apparatus; and a controller communicatively connected to the imaging apparatus and configured to: receive a capturing parameter corresponding to a sample appearance image of the sample slide to be tested, and control the imaging apparatus to capture, with the capturing parameter, images of sample components on the sample slide to be tested, where the sample appearance image includes at least an appearance image of the sample film.

In addition, a third aspect of the disclosure further provides a sample image capturing method, including:

obtaining, from a sample appearance image obtaining apparatus, a sample appearance image of a side of the sample slide to be tested, on which side the sample film to be tested is applied, where the sample appearance image includes at least an appearance image of the sample film;

identifying an appearance characteristic of the sample film based on the sample appearance image and determining a capturing parameter based on the appearance characteristic; and controlling an imaging apparatus to capture, with the capturing parameter, images of sample components in the sample film on the sample slide to be tested.

A fourth aspect of the disclosure provides a computer-readable storage medium storing executable instructions stored thereon, and the executable instructions, when executed by a computer, cause the computer to implement the steps of the sample image capturing method provided in accordance with the third aspect of the disclosure.

In the disclosure, the appearance characteristic of the sample film is obtained based on the sample appearance image of the side of the sample slide to be tested, on which side the sample film to be tested is applied, especially the appearance image of the sample film, and then the capturing parameter of the imaging apparatus is determined based on the appearance characteristic of the sample film, so that the imaging apparatus can accurately capture, with the capturing parameter, images of sample components such as cells in the sample film such as a blood film on the sample slide to be tested.

For other features and advantages of the aspects of the disclosure, reference may be made to the following description of the embodiments of the disclosure in conjunction with the accompanying drawings.

DETAILED DESCRIPTION

The technical solutions in the embodiments of the disclosure will be described below clearly and completely in conjunction with the accompanying drawings in the embodiments of the disclosure. The embodiments described are merely some rather than all of the embodiments of the disclosure. Based on the embodiments in the disclosure, all the other embodiments that would have been obtained by those of ordinary skill in the art without any inventive effort shall fall within the scope of protection of the disclosure.

The serial numbers themselves for the components herein, for example, "first" and "second", are merely used to distinguish the described objects, and do not have any sequential or technical meaning. Moreover, as used in the disclosure, "connection" or "coupling", unless otherwise stated, includes both direct and indirect connections (couplings). In the description of the disclosure, it should be understood that the orientation or position relationship indicated by the terms "upper", "lower", "front", "rear", "left", "right", "vertical" "horizontal", "top", "bottom", "inner", "outer", "clockwise", "counterclockwise" etc. are based on the orientation or position relationship shown in the accompanying drawings and are intended to facilitate the description of the disclosure and simplify the description only, rather than indicating or implying that the apparatus or element referred to must have a particular orientation or be constructed and operated in a particular orientation, and therefore will not to be interpreted as limiting the disclosure.

As mentioned in the background, not all sample slides are very standard, that is, sample films (or sample smear layers) on the sample slides vary in form, for example, some of which are long while some are short. As a result, appropriate or desired capturing positions and/or capturing regions on the sample slides may be different.

Figure 1:
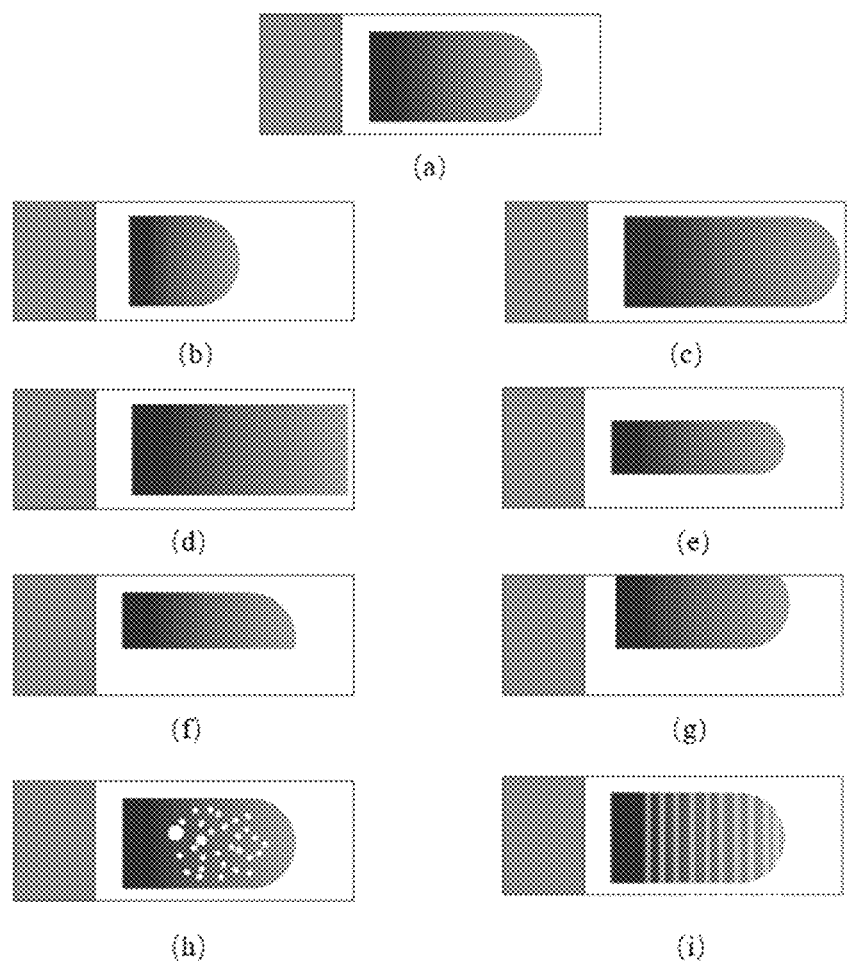
FIG. 1 is a schematic diagram of blood smears with different smearing states.

For example, microscope slides (sample slides) with sample films can be prepared by a slide maker, which prepares a sample slide through processes such as sample collection, sample smearing or spreading, drying, staining, and washing. The slide maker has strict requirements in clinical examination, and it is usually necessary to control the slide maker by using sample characteristics (such as an HCT value, a viscosity characteristic, a residual tailing characteristic, etc.) as preparation parameters. An exception of the slide maker directly affects the progress and accuracy of microscopic examination of a sample. In addition to the above-mentioned factors such as the HCT value, the viscosity characteristic, the residual tailing characteristic, etc. that may result in an exception the slide maker, a working status of respective components of the slide maker, sanitation of related components, and detection accuracy of sensors may all cause an exception of slide making or staining. For example, FIG. 1(a) is a schematic diagram of a normal blood sample slide. Cases that do not meet expectations of blood smear preparation include: a shorter blood film shown in FIG. 1(b), a longer blood film shown in FIG. 1(c), an excessively long blood film shown in FIG. 1(d), an excessively narrow blood film shown in FIG. 1(e), an incomplete blood film shown in FIG. 1(f), a blood film with deviation to one side shown in FIG. 1(g), a blood film with holes shown in FIG. 1(h), or a blood film with stripes shown in FIG. 1(i).

It can be seen that, if a uniform capturing mode such as a uniform capturing position and/or a uniform capturing region is used, it is possible that the captured sample images are inappropriate, or even no sample image can be captured.

Therefore, the embodiments of the disclosure propose a solution, in which whether there is an exception in application of a sample film or preparation of a sample slide is identified based on an appearance image of the sample film side of the sample slide; for example, a length, width, and tail shape of the sample film, or even whether the sample film has holes, scratches, or stripes can be identified; and then image capturing by an imaging apparatus can be adjusted specifically based on position characteristic and/or distribution characteristic of the sample film.

Figure 2:
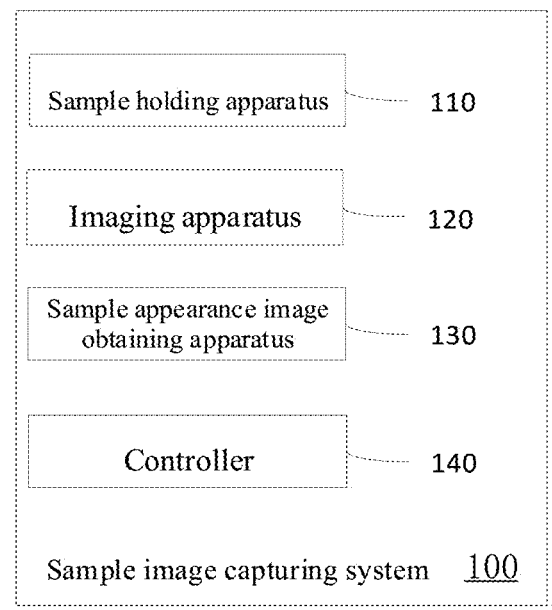
FIG. 2 is a schematic block diagram of a sample image capturing system according to an embodiment of the disclosure.

To this end, as shown in FIG. 2, the disclosure first provides a sample image capturing system 100, the sample image capturing system 100 includes a sample holding apparatus 110, an imaging apparatus 120, a sample appearance image obtaining apparatus 130, and a controller 140.

The sample holding apparatus 110 is configured to hold or support a sample slide 10 to be tested on which a sample film 11 to be tested is applied. The sample holding apparatus 110 may be, for example, configured to be arranged opposite to the imaging apparatus 120 and to be movable relative to the imaging apparatus 120, such that the imaging apparatus 120 can capture images of sample components in a specific region of the sample film 11 on the sample slide 10 supported on the sample holding apparatus 110.

Figure 3:
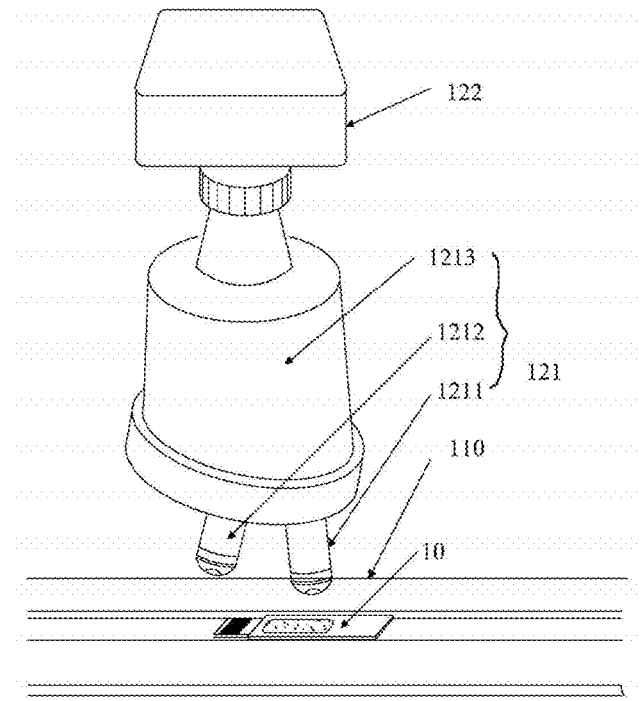
FIG. 3 is a schematic structural diagram of an imaging apparatus according to an embodiment of the disclosure.

In some embodiments, as shown in FIG. 3, the sample holding apparatus 110 is, for example, configured as a test table movable in a horizontal plane, and the test table may have a groove for receiving the sample slide 10. In some other embodiments, the sample holding apparatus 110 may alternatively be configured as a robotic arm movable at least horizontally, and the robotic arm has a gripper for gripping the sample slide 10.

The imaging apparatus 120 is configured to capture images of the sample on the sample slide to be tested that is held by the sample holding apparatus 110, to obtain sample component images. For example, when the sample is a blood sample, the sample slide is a blood smear on which a blood film is applied, and sample components are particles such as cells in the blood sample. In this case, the imaging apparatus 120 is configured to capture images of cells in the blood film on the blood smear. Certainly, the sample in the disclosure may also be bone marrow, body fluids, etc.

In some embodiments, as shown in FIG. 3, the imaging apparatus 120 may also be referred to as a microscopic optical module. The microscopic optical module includes a lens group 121 and a first camera 122, and the lens group 121 may include a first objective lens 1211 and a second objective lens 1212. The first objective lens 1211 may be, for example, a 10× objective lens or a 40× objective lens, and the second objective lens 1212 may be, for example, a 40× objective lens or a 100× objective lens. The lens group 121 may further include a switching mechanism 1213. The switching mechanism is configured to switch between the first objective lens 1211 and the second objective lens 1212, so that the first camera 122 captures sample component images with different magnifications.

Certainly, in other embodiments, the imaging apparatus 120 may include only the first camera, that is, the arrangement of the lens group may be omitted.

The sample appearance image obtaining apparatus 130 is configured to obtain a sample appearance image 20 of a side of the sample slide 10 to be tested, on which side the sample film 11 to be tested is applied, wherein the sample appearance image at least includes an appearance image of the sample film.

Figure 4:
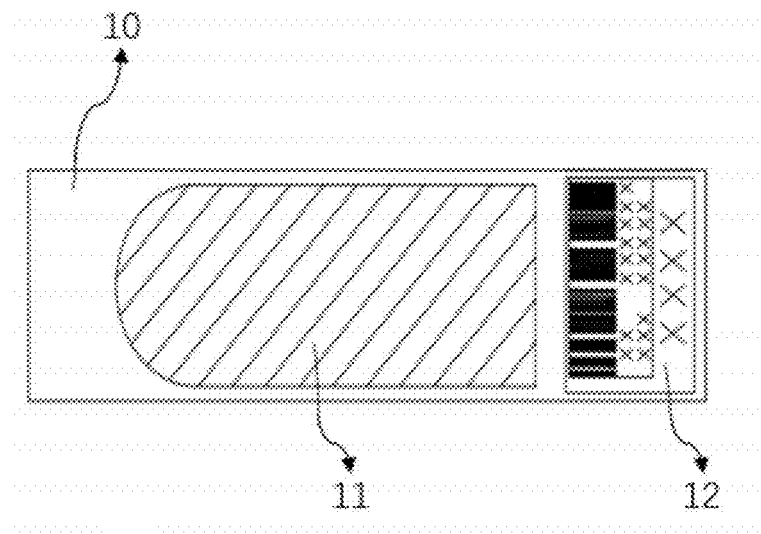
FIG. 4 is a schematic structural diagram of a sample slide according to an embodiment of the disclosure.
Figure 5:
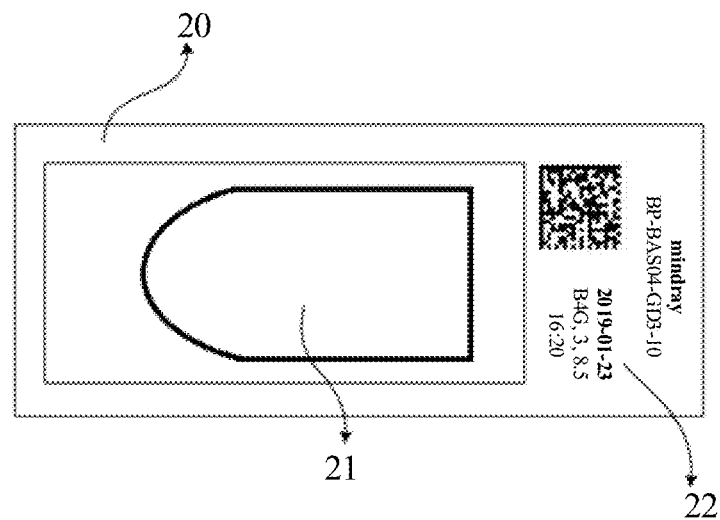
FIG. 5 is an appearance image of a sample slide according to an embodiment of the disclosure.

As shown in FIGS. 4 and 5, the sample film 11 such as a blood film is applied on the sample slide 10, and the sample appearance image 20 includes at least an appearance image 21 of the sample film. In addition, the sample film side of the sample slide 10 may be further provided with a sample identification portion 12, such as a barcode label, and the sample appearance image 20 may also include an appearance image 22 of the sample identification portion 12.

Figure 6:
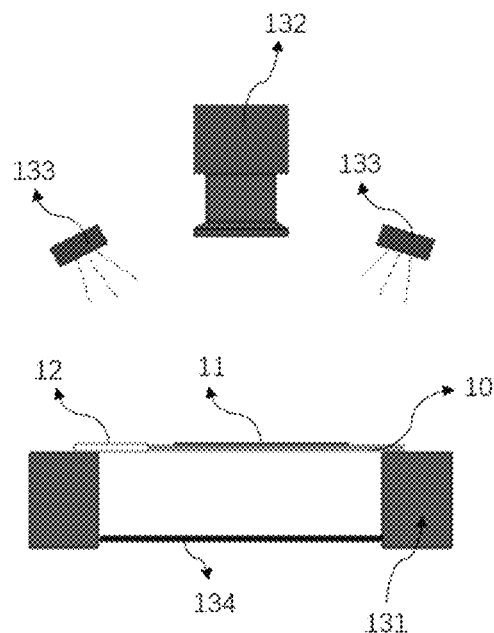
FIG. 6 is a schematic structural diagram of a sample appearance image obtaining apparatus according to an embodiment of the disclosure, where a sample slide support apparatus horizontally supports a sample slide.
Figure 7:
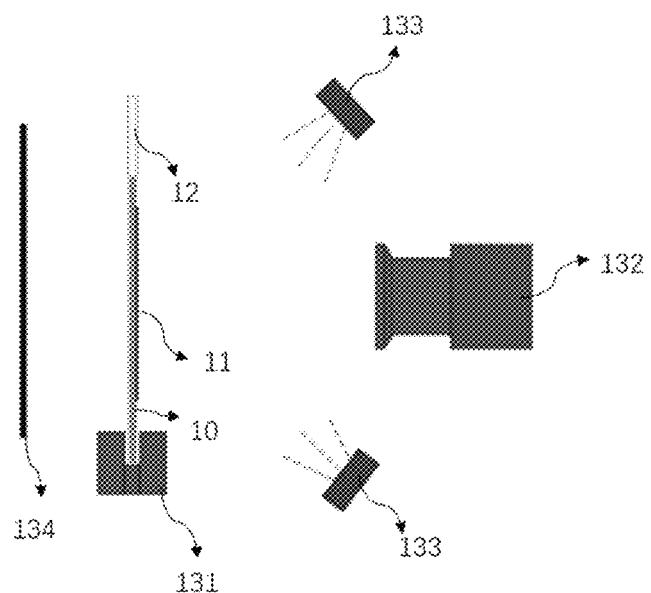
FIG. 7 is a schematic structural diagram of a sample appearance image obtaining apparatus according to an embodiment of the disclosure, where a sample slide support apparatus vertically supports a sample slide.

In some embodiments, the sample appearance image obtaining apparatus 130 may include a second camera 132, for example, including an image sensor and an imaging lens. As shown in FIGS. 6 and 7, the sample appearance image obtaining apparatus 130 may include a sample slide support apparatus 131 configured to support the sample slide 10, so that the sample slide 10 is at a specific distance or space from the second camera 132. The second camera 132 is arranged opposite to the sample slide support apparatus 131, so that the second camera 132 can capture an appearance image of the sample slide 10 supported on the sample slide support apparatus 131. The sample slide support apparatus 131 may be configured to horizontally support the sample slide 10, as shown in FIG. 6. Alternatively, the sample slide support apparatus 131 may vertically support the sample slide 10, as shown in FIG. 7.

In the embodiments shown in FIGS. 6 and 7, the sample appearance image obtaining apparatus 130 further includes a lighting source 133 and a background plate 134, such as a solid-colored non-reflective background plate. The lighting source is configured to irradiate the sample slide 10 on the sample slide support apparatus 131 with light, to provide suitable illumination for the capturing by the second camera 132, so as to obtain a sharp and bright appearance image of the sample slide. Herein, the lighting source 133 and the second camera 132 are arranged at one side of the sample slide 10, that is, the side facing the sample film 11 on the sample slide 10, and the background plate 134 is arranged at the other side of the sample slide 10 to provide a homogeneous background free from interference or stray light. It may be understood that the arrangement of the lighting source 133 and the background plate 134 may also be omitted.

Figure 8:
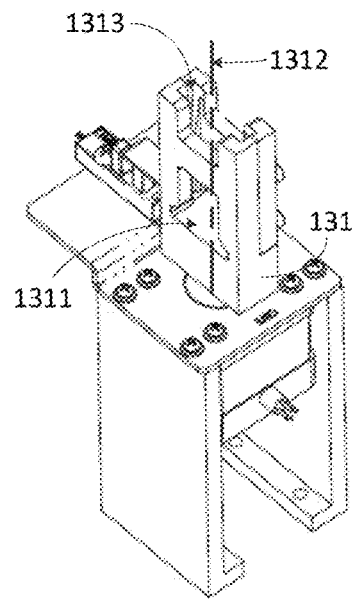
FIGS. 8 and 9 are schematic structural diagrams of a sample appearance image obtaining apparatus according to an embodiment of the disclosure.
Figure 9:
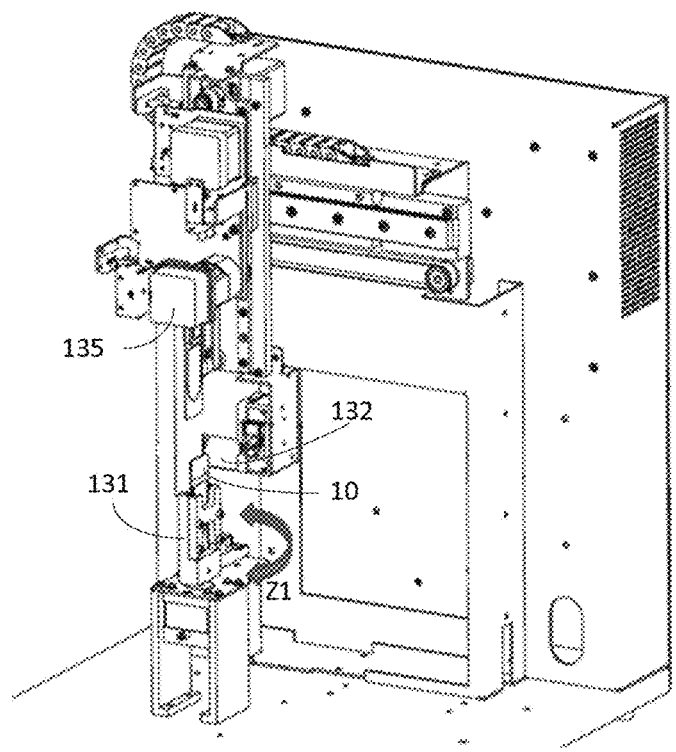

FIGS. 8 and 9 are schematic structural diagrams of a sample slide support apparatus 131 vertically supporting the sample slide 10. The sample slide support apparatus 131 includes an accommodation slot 1311 having an opening on the top. The accommodation slot 1311 is configured to accommodate the sample slide 10. The accommodation slot 1311 extends along a central axis 1312 of the sample slide support apparatus 131, the top of the accommodation slot 1311 is provided with an opening 1313, and the sample slide 10 is placed into the accommodation slot 1311 from the opening 1313.

In order to obtain an appearance image of the side of the sample slide 10 on which the sample film is applied, in some embodiments, one side of the accommodation slot 1311 is opened toward the outside, so that the side of the sample slide 10 with the sample film applied is exposed to the outside, and the second camera 132 can capture the appearance image of the sample slide 10.

Further, in some embodiments, the sample slide support apparatus 131 is configured to be rotatable at least 180 degrees in a predetermined rotation direction so as to drive the accommodated sample slide 10 to rotate at least 180 degrees in the predetermined rotation direction about an axis extending in a lengthwise direction of the sample slide 10, so that the sample film side of the sample slide 10 accommodated in the sample slide support apparatus 131 can always be placed within a capturing range of the second camera 132.

In some alternative embodiments, side surfaces of the accommodation slot 1311 may be closed. A slide gripping apparatus 135, such as a robotic arm, is provided to grip up the sample slide 10 from the accommodation slot 1311 of the sample slide support apparatus 131, so that the sample film side of the sample slide 10 is within the capturing range of the second camera 132, to capture the appearance image of the sample film side of the sample slide 10.

It may be understood that the slide gripping apparatus 135 may be configured to be rotatable at least 180 degrees about its own axis to drive the gripped sample slide 10 to rotate, so that the sample film side of the sample slide 10 can always be placed within the capturing range of the second camera 132.

Preferably, the first camera 122 and the second camera 132 are different, that is, the second camera 132 and the first camera 122 are independent of each other.

Certainly, in other embodiments, the first camera 122 may be used as the second camera 132 at the same time. In this case, the second camera 132 captures images of a plurality of regions of the sample film on the sample slide 10, and then the images of the plurality of regions are spliced into an image that can represent an appearance of the sample film.

In addition, in some embodiments, the sample appearance image obtaining apparatus 130 may also be, for example, a software module integrated into the controller to be further described below. In this case, the sample appearance image obtaining apparatus 130 is configured to obtain a sample appearance image from a camera that captures the sample appearance image of the sample slide 10.

The controller 140 is connected to the imaging apparatus 120 to control the imaging apparatus 120 to capture imaged of sample components such as cells in the sample film 11 on the sample slide 10. In addition, the controller 140 is communicatively connected to the sample appearance image obtaining apparatus 130 to obtain the sample appearance image. Herein, the controller 140 is configured to: obtain the sample appearance image from the sample appearance image obtaining apparatus, identify an appearance characteristic of the sample film based on the sample appearance image, determine a capturing parameter based on the appearance characteristic, and control the imaging apparatus to capture, with the capturing parameter, images of sample components in the sample film on the sample slide to be tested.

Figure 10:
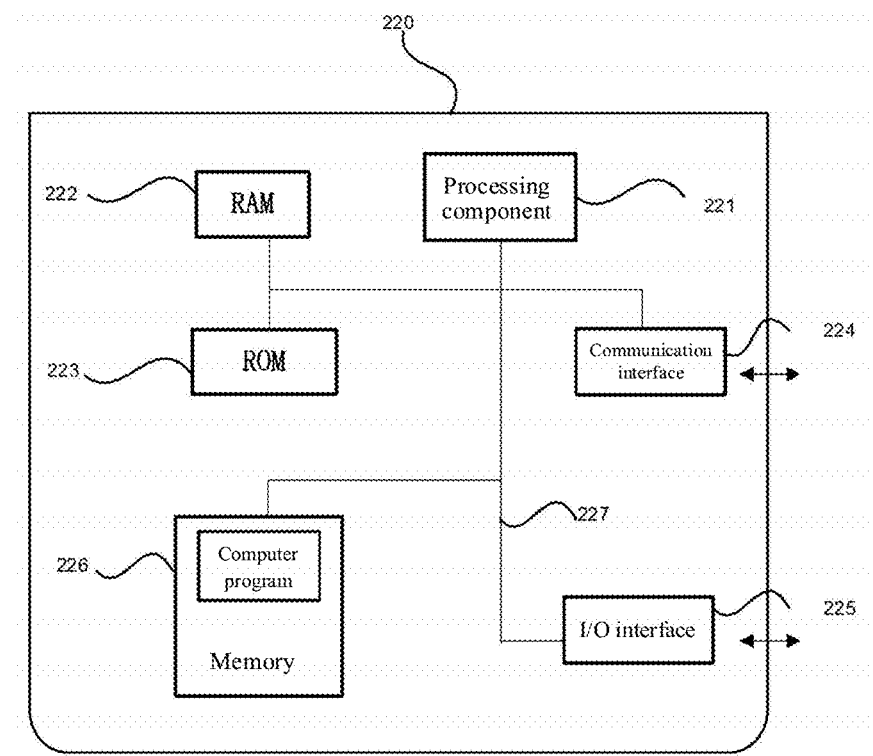
FIG. 10 is a schematic block diagram of a controller according to an embodiment of the disclosure.

As shown in FIG. 10, the controller 140 may include, for example, a processing component 221, a RAM 222, a ROM 223, a communication interface 224, a memory 226, and an I/O interface 225, wherein the processing component 221, the RAM 222, the ROM 223, the communication interface 224, the memory 226, and the I/O interface 225 communicate with each other via a bus 227.

The processing component may be a CPU, a GPU, or another chip having a computing capability. The memory 226 contains an operating system, and various computer programs such as an application program executable by the processing component 221, and data required for execution of the computer programs.

The I/O interface 225 is composed of a serial interface such as USB, IEEE 1394, or RS-232C, a parallel interface such as SCSI, IDE, or IEEE 1284, and an analog signal interface composed of a D/A converter and an A/D converter, etc. An input device composed of a keyboard, a mouse, a touchscreen, or another control button is connected to the I/O interface 225, and a user may directly input data to the controller 240 by using the input device.

The communication interface 224 may be an interface of any communication protocol currently known. The communication interface 224 communicates with the outside over a network. The controller 140 may exchange, through the communication interface 224 and based on a communication protocol, data with any apparatus connected over the network.

In addition, the sample image capturing system 100 may further include a sample identity obtaining apparatus 150 configured to obtain sample identity information of the sample slide 10. The sample identity obtaining apparatus 120 may be hardware such as a barcode scanner for scanning a barcode label, or a software module such as a software module integrated into the controller to be further described below, which is not specifically limited in the disclosure. In addition, the sample identity information may be label information on the sample slide, or may be randomly assigned or temporary information, as long as different sample slides can be distinguished, which is not specifically limited in the disclosure, either.

In some embodiments, the sample identity obtaining apparatus 150 is a barcode scanner, and the second camera 132 is integrated into the sample identity obtaining apparatus 150 configured as a barcode scanner, that is, the sample identity obtaining apparatus 150 is configured as a barcode scanner with a camera. The barcode scanner with a camera is arranged opposite to the sample slide support apparatus 131 such that the barcode scanner with a camera can scan the sample identification portion, such as a barcode label, of the sample slide 10 supported on the sample slide support apparatus 131, and at the same time, can capture the image of the sample film side of the sample slide 10.

Figure 11:
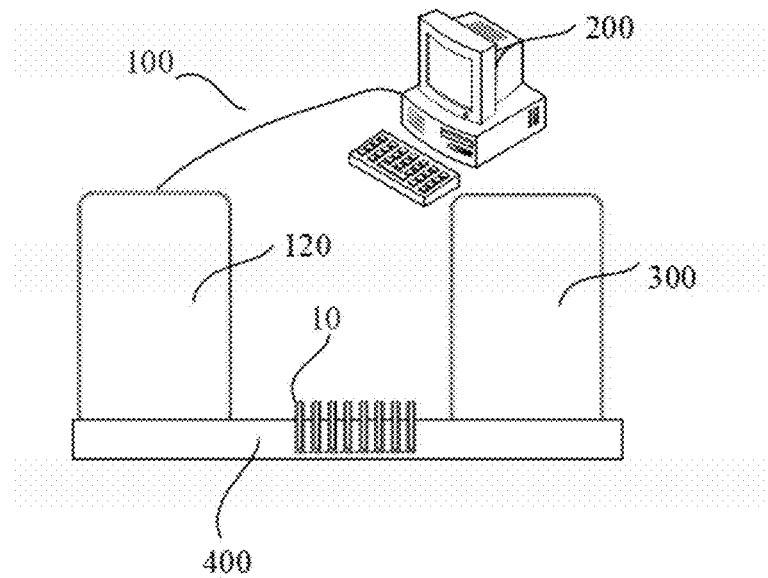
FIG. 11 is a schematic structural diagram of a sample image capturing system according to an embodiment of the disclosure.

In addition, as shown in FIG. 11, the sample image capturing system 100 may further include a display apparatus 200 configured to display at least the appearance image of the sample film. Certainly, the display apparatus may also be enabled to display an overall appearance image of the entire sample slide including the sample film. Further, the sample identity information and the sample component images of the sample slide may be further displayed on the display apparatus. In some embodiments, the display apparatus may be connected to the I/O interface 225 of the controller, the display apparatus may be, for example, a liquid crystal display, a touchscreen, an LED display, etc., and the controller may cause the display apparatus to display the appearance image, the sample component images, etc. of the sample slide in association with the sample identity information.

Further, as shown in FIG. 11, the sample image capturing system 100 further includes a sample slide preparation apparatus (also referred to as a slide maker) 300 and a transport apparatus 400. The sample slide preparation apparatus 300 is configured to apply a sample to a clean slide to form a sample slide, for example, smear a blood sample on the clean slide to form a blood smear. The transport apparatus 400 is configured to transport the sample slide 10 prepared by the sample slide preparation apparatus 300 to the imaging apparatus 120. The transport apparatus 400 may be, for example, a track, and the sample slide preparation apparatus 300 transports a prepared sample slide to an entrance to the imaging apparatus 120 through the track.

In the embodiment of FIG. 11, the second camera 132 may be arranged in the sample slide preparation apparatus 300 or on a path along which the sample slide is transported by the transport apparatus 400.

The following describes how to use the sample appearance image, especially the appearance image of the sample film, to guide the image capturing by the imaging apparatus 120.

In an embodiment of the disclosure, the controller 140 is configured to obtain and analyze the appearance image of the sample slide, and control the imaging apparatus 120 to capture images of sample components in the sample film 11 based on the analysis result. In this way, the appearance image of the sample slide, especially the appearance image of the sample film, can be used to guide the image capturing by the imaging apparatus 120, so that desired sample component images can be accurately captured, and automation and intelligence of the sample image capturing system can be improved.

In some embodiments, the appearance characteristic of the sample film includes at least one of a position characteristic and a distribution characteristic of the sample film on the sample slide to be tested. In the embodiments of the disclosure, the position characteristic may include position information of boundaries of the sample film formed on the sample slide to be tested and/or position information of a specific region of the sample film formed on the sample slide to be tested, for example, including position information of two edges of the sample film on the sample slide, etc. The distribution characteristic may include thickness information of the sample film formed on the sample slide to be tested, and information indicating whether the sample film has holes, stripes, etc.

Specifically, the appearance characteristic of the sample film may include but is not limited to characteristics such as shape, contour, area, position, color, grayscale, width, and length.

In a specific example, the appearance characteristic of the sample film includes the position characteristic of the sample film on the sample slide to be tested, and a position of a region of interest in the sample film, that is, a position of a region to be captured, is determined based on the position characteristic, so as to guide the imaging apparatus 120 to capture images of sample components in the capturing region of interest at the determined position. In other words, the controller 140 is configured to determine a position of a capturing region of interest of the sample film on the sample slide to be tested based on the appearance characteristic (in this case, the capturing parameter is position information of the capturing region of interest on the sample slide to be tested), and control the imaging apparatus 120 to capture images of the capturing region of interest, and in particular, control the sample holding apparatus 110 to move relative to the imaging apparatus 120, so that the imaging apparatus 120 can capture images of sample components within the capturing region of interest at the determined position. In this way, the position to be scanned and captured can be directly located, that is, the capturing region of interest can be directly located, which avoids large-range scanning during image capturing and avoids an increase in futile capturing time, so that the sample image capturing system 100 can automatically and accurately obtain sample component images in the capturing region of interest, without increasing an image capturing range to ensure that the capturing region of interest is captured, and therefore the image capturing speed can also be increased.

Herein, the capturing region of interest may include, for example, contour edges of the sample film 11. For example, when the sample is a blood sample, a blood film with a tail portion of a specific shape is formed after the blood sample is applied to a slide. In this case, a position of the tail portion on the blood smear and the contour edges can be identified by analyzing the appearance image of the sample slide, so that the imaging apparatus 120 can capture images of the tail portion of the blood film in a targeted manner. For another example, when the sample is a body fluid sample, the body fluid sample is usually applied to the middle of a slide. However, due to differences in preparation of sample slides, there may be deviations in application of body fluid samples. A position of the body fluid sample on the sample slide can be accurately identified by using the appearance image of the sample slide of the disclosure, and the imaging apparatus 120 can accurately capture images of the body fluid sample on the sample slide.

Figure 12:
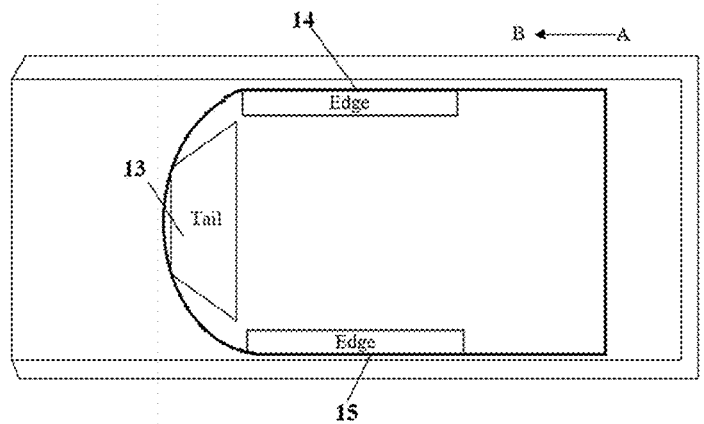
FIG. 12 is a schematic diagram of a blood smear according to an embodiment of the disclosure.

In a specific example, as shown in FIG. 12, when the sample slide is a slide smeared with a blood sample, the blood film sequentially includes a head portion, a body portion, and a tail portion on the sample slide in a smearing direction (an arrow direction from A to B). The capturing region of interest includes at least one of the tail portion 13 and an edge portion 14 and 15 of the blood film. Due to differences in shapes of blood films smeared on slides, a position of the capturing region of interest such as the tail portion and the edge portion also changes. Therefore, generally, only an approximate position of the capturing region of interest can be known in advance. If a fixed position of the capturing region of interest is preset, it is possible that images of the capturing region of interest cannot be captured completely, or even no images of the capturing region of interest can be captured, and important information of the sample slide is thus missing, which may hinder a physician in making accurate clinical judgments. Therefore, the appearance image of the sample film side of the sample slide that is obtained in the disclosure is used to analyze the position of the sample film on the sample slide and the contour of the sample film, and then the position of the capturing region of interest on the sample slide can be obtained, so that the imaging apparatus 120 can capture images of the capturing region of interest in a targeted manner.

Further, to determine the capturing region of interest of the sample film on the sample slide to be tested, the sample image capturing system 100 further includes a mode obtaining apparatus 160 configured to obtain a capturing mode for the sample slide to be tested. The capturing mode includes information about the capturing region of interest of the sample slide to be tested. And the controller 140 is further communicatively connected to the mode obtaining apparatus and is further configured to: before determining the position of the capturing region of interest, obtain the capturing mode for the sample slide to be tested from the mode obtaining apparatus, and determine the capturing region of interest based on the capturing mode.

In some embodiments, the sample slide to be tested is further provided with a label containing sample identity information, and the sample identity information is associated with the capturing mode for the sample slide to be tested. The mode obtaining apparatus is configured to obtain, from the label of the sample slide to be tested, the sample identity information of the sample slide to be tested. Herein, the controller 140 is configured to obtain, based on the sample identity information obtained from the mode obtaining apparatus, the capturing mode for the sample slide to be tested. The mode obtaining apparatus may be, for example, the foregoing sample identity obtaining apparatus.

In some embodiments, the controller 140 is further communicatively connected to a hematology analyzer or a central controller, the central controller being communicatively connected to the hematology analyzer, so that the controller can obtain the capturing mode for the sample slide to be tested from the hematology analyzer or the central controller based on the sample identity information obtained from the mode obtaining apparatus, wherein the capturing mode for the sample slide to be tested is obtained by the hematology analyzer by testing a sample from same subject as the sample on the sample slide to be tested and is stored in the hematology analyzer or the central controller in association with the sample identity information of the sample slide to be tested.

Herein, the hematology analyzer is a device configured to perform a routine blood test on a blood sample to be tested or a body fluid sample to be tested. When the hematology analyzer tests a sample to be tested and finds through analysis that the sample to be tested is abnormal and needs to be further microscopically examined by the sample image capturing system, a capturing mode corresponding to the abnormality of the sample to be tested is then stored in the hematology analyzer or the central controller connected to the hematology analyzer in association with identity information of the sample to be tested, so that the controller of the sample image capturing system can obtain the capturing mode from the hematology analyzer or the central controller based on the identity information of the sample to be tested, and then obtain the capturing region of interest based on the obtained capturing mode.

In some specific embodiments, the sample to be tested is a blood sample, the sample slide to be tested is a blood smear smeared with a blood film, and the blood film sequentially includes a head portion, a body portion, and a tail portion on the blood smear in a smearing direction and further comprises two edge portions. Herein, the controller 140 is configured to: when the capturing mode obtained from the mode obtaining apparatus is a platelet capturing mode, determine that the capturing region of interest includes at least one of the edge portions and the tail portion of the blood film based on the platelet capturing mode, determine a position of the at least one of the edge portions and the tail of the blood film based on the appearance characteristic, and control the imaging apparatus to capture, at the determined position, images of sample components in the at least one of the edge portions and the tail portion of the blood film. For example, when the sample to be tested has a platelet abnormality, the capturing mode is the platelet capturing mode, and the capturing region of interest corresponding to the platelet capturing mode includes the edge portions and/or the tail portion of the blood film (because there is relatively high probability that platelets appear in the edge portions and/or the tail portion of the blood film). In this case, the controller 140 determines a position of the edge portions and/or the tail portion of the blood film on the blood smear by analyzing the appearance image of the blood film, and then controls the sample holding apparatus 110 to move relative to the imaging apparatus 120, so that the imaging apparatus 120 can accurately capture images of the edge portions and/or the tail portion of the blood film.

Further, the controller 140 is configured to: when the capturing mode obtained from the mode obtaining apparatus is a white-blood-cell capturing mode, determine the body portion of the blood film as the capturing region of interest based on the white-blood-cell capturing mode, determine a position of the body portion of the blood film based on the appearance characteristic, and control the imaging apparatus to capture, at the determined position, images of sample components in the body portion of the blood film. For example, when the sample to be tested has a white blood cell abnormality, the capturing mode is the white-blood-cell capturing mode, and the capturing region of interest corresponding to the white-blood-cell capturing mode includes the body portion of the blood film. In this case, the controller determines a position and an appropriate capturing range of the body portion of the blood film on the blood smear by analyzing the appearance image of the blood film, and then controls the sample holding apparatus 110 to move relative to the imaging apparatus 120, so that the imaging apparatus 120 can accurately capture images of the region of the body portion of the blood film.

In addition, the controller 140 is further configured to: when the capturing mode obtained from the mode obtaining apparatus is a body-fluid mode, determine that the capturing region of interest is the entire sample film on the sample slide to be tested based on the body-fluid mode, determine a position and a contour boundary of the sample film based on the appearance characteristic, and control the imaging apparatus to capture, based on the determined position and the determined contour boundary, images of the entire sample film on the sample slide to be tested. For example, when the sample to be tested is a body fluid sample, the capturing mode is the body-fluid capturing mode, and the capturing region of interest corresponding to the body-fluid capturing mode is the entire sample film. In this case, the controller analyzes determines a position and a boundary of the entire sample film on the sample slide to be tested by analyzing the sample appearance image, and controls the sample holding apparatus 110 to move relative to the imaging apparatus 120, so that the imaging apparatus 120 can accurately capture images of the entire sample film.

Alternatively or additionally, the controller 140 is configured to determine a capturing path and/or a capturing range of the sample film on the sample slide to be tested based on the appearance characteristic of the sample film, and control the imaging apparatus 120 to capture images of the sample film on the sample slide to be tested based on the determined capturing path and/or capturing range.

Therefore, according to the disclosure, a proper capturing position and capturing region of the sample film can be identified based on the position characteristic and/or the distribution characteristic extracted from the sample appearance image, so that desired sample component images can be accurately obtained, false alarms can be reduced, and the sample image capturing speed can be increased.

In some embodiments, the sample appearance image according to the disclosure can be further used to identify a sample type (peripheral blood sample, bone marrow sample, body fluid sample, malaria sample, etc.), so as to select a corresponding capturing mode (peripheral blood mode, bone marrow mode, body fluid mode, malaria mode, etc.) based on the sample type. Herein, for example, it may be determined whether the sample to be tested is a peripheral blood sample, a body fluid sample, or a bone marrow sample based on an appearance shape, a contour, an area, and other characteristics of the sample film on the sample slide to be tested.

In other words, the controller 140 may be further configured to identify or determine a sample type of the sample film 11 based on the appearance characteristic of the appearance image 20 of the sample slide 10, determine the capturing parameter based on the sample type of the sample film and control the imaging apparatus 120 to capture images of sample components in the sample film with the capturing parameter corresponding to the sample type of the sample film 11. Therefore, the type of the sample slide to be tested can be automatically identified and the capturing mode can be automatically adjusted accordingly, so that a required capturing mode can be automatically performed for different types of sample slides.

Different types of samples usually have different requirements on microscopic examination, such as different image capturing regions or different image capturing numbers, etc. Therefore, a type of a sample usually needs to be known before the imaging apparatus captures sample component images of the sample. The appearance image of the sample film side of the sample slide obtained in the disclosure can be used to identify the sample type. This is particularly advantageous when the sample image capturing system cannot obtain identity label information on the sample slide, and this can ensure that sample component images of the sample slide are properly captured according to a normal procedure, without issuing alarms or stopping image capturing.

In some embodiments, capturing parameters corresponding to different types of samples may be preset by a user and stored in a memory of the controller 140 or stored in a memory of the central controller communicatively connected to the controller 140. After determining the type of the sample slide to be tested, the controller 140 automatically calls a capturing parameter set by the user, so as to control the imaging apparatus 120 to capture images of the sample slide to be tested based on the user's requirements. In this case, the sample image capturing system 100 may have, for example, a user setting interactive interface, to receive and store different capturing parameters (for example, image capturing region or image capturing number) of the user. When the controller 140 has identified different sample types, the controller automatically selects the user's preset capturing parameters to control the imaging apparatus 120 to perform scanning and image capturing based on the preset capturing parameters.

Certainly, in other embodiments, the capturing parameters corresponding to different types of samples may alternatively be preset and stored by a device manufacturer.

Alternatively or additionally, the sample image capturing system 100 includes an oil applying apparatus (not shown in the figure) configured to apply oil (for example, cedar oil) on the sample slide to be tested that is held by the sample holding apparatus, wherein the capturing parameter includes information about whether to apply oil.

When the first camera 122 of the imaging apparatus 120 captures images of the sample slide to be tested under a high-power objective lens 1212 (or an oil immersion lens), such as a 40× objective lens or a 100× objective lens, of the imaging apparatus 120, it is usually necessary to use the oil applying apparatus to apply cedar oil on the sample slide to be tested. This is because magnification of the oil immersion lens is high, and the lens is small. When light passes through medium objects with different densities, part of the light may be refracted and lost, less light enters a lens barrel, visual brightness is relatively low, and an object cannot be viewed clearly. If cedar oil is applied between the high-power lens and the sample slide to be tested, more light enters the oil immersion lens, visual brightness is enhanced, and an object image is sharp.

Therefore, in this embodiment of the disclosure, whether oil has been applied on the sample film side of the sample slide to be tested may be further determined based on the sample appearance image, so as to determine whether the oil applying apparatus needs to be used currently to apply oil on the sample slide to be tested. In other words, the controller 140 is configured to: when it is determined to apply oil on the sample slide to be tested based on the appearance characteristic, control the oil applying apparatus to apply oil on the sample slide to be tested before controlling the imaging apparatus to perform image capturing (especially under a high-power objective lens). This is particularly advantageous when a sample slide that has already been captured by the imaging apparatus 120 is captured again, and this can avoid applying oil again on a sample slide that has been applied with cedar oil.

Alternatively or additionally, in an embodiment of the disclosure, whether the sample slide to be tested meets capturing requirements may be further determined based on the sample appearance image, and an alarm is issued for a sample slide that may affect an analysis result or is not suitable for capturing. For example, an alarm is output when it is determined, based on the sample appearance image, that the slide maker has an exception, there is no sample smear layer, the slide is damaged, or the sample type does not match the sample identity. In this case, preferably, the imaging apparatus 120 no longer captures images of the abnormal sample slide to be tested.

The following describes a sample image capturing method 1000 according to the disclosure. The sample image capturing method 1000 is implemented in particular by various embodiments of the sample image capturing system 100 described above. In particular, the sample image capturing method 1000 is implemented by the controller 140 of the sample image capturing system 100.

Figure 13:
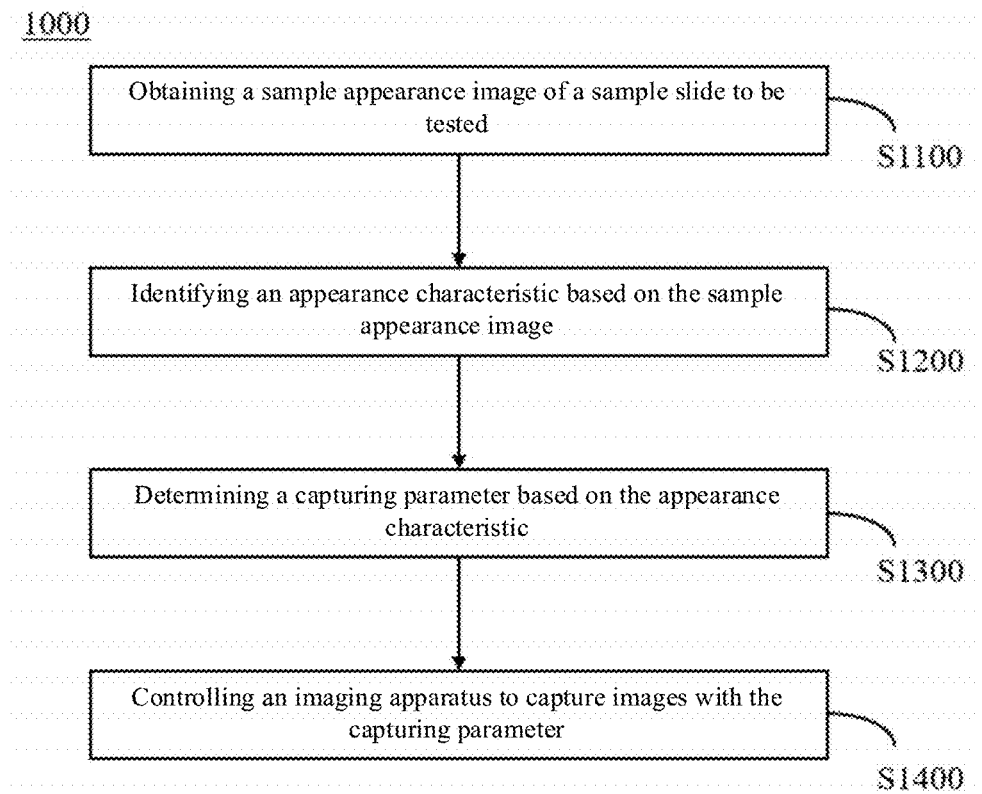
FIG. 13 is a schematic flowchart of a sample image capturing method according to an embodiment of the disclosure.

As shown in FIG. 13, the sample image capturing method 1000 includes the following steps:

In S1100, a sample appearance image 20 of a side of a sample slide 10 to be tested, on which side a sample film 11 to be tested is applied, is obtained, wherein the sample appearance image 20 includes at least an appearance image 21 of the sample film 11. In this step, the sample appearance image 20 is obtained from the sample appearance image obtaining apparatus 130.

In S1200, an appearance characteristic of the sample film is identified based on the sample appearance image 20.

In S1300, a capturing parameter is determined based on the appearance characteristic.

In S1400, the imaging apparatus 120 is controlled to capture, with the capturing parameter, images of sample components in the sample film on the sample slide to be tested.

Therefore, the capturing parameter can be automatically adjusted based on the appearance characteristic obtained from the appearance image of the sample film, also referred to as sample smear layer, so as to improve image capturing efficiency and accuracy.

Figure 14:
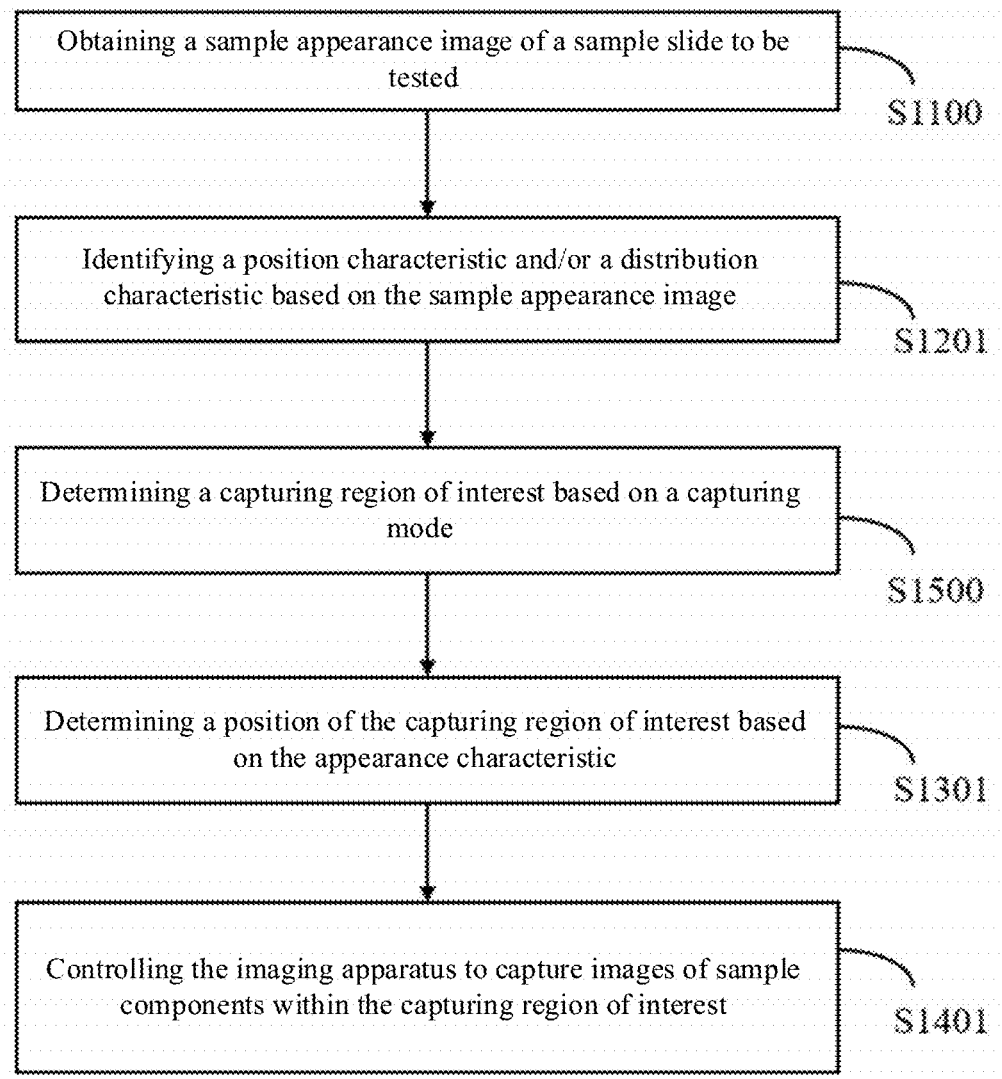
FIG. 14 is a schematic flowchart of a sample image capturing method according to another embodiment of the disclosure.

In some embodiments, as shown in FIG. 14, step S1200 may include step S1201: identifying at least one of a position characteristic and a distribution characteristic of the sample film on the sample slide to be tested based on the sample appearance image. Correspondingly, step S1300 may include step S1301: determining a position of a capturing region of interest of the sample film on the sample slide to be tested based on the appearance characteristic. Step S1400 may include step S1401: controlling the imaging apparatus to capture images of sample components within the capturing region of interest at the determined position.

Further, as shown in FIG. 14, before step S1301, the sample image capturing method 1000 includes step S1500: obtaining a capturing mode for the sample slide to be tested, and determining the capturing region of interest based on the capturing mode.

Figure 15:
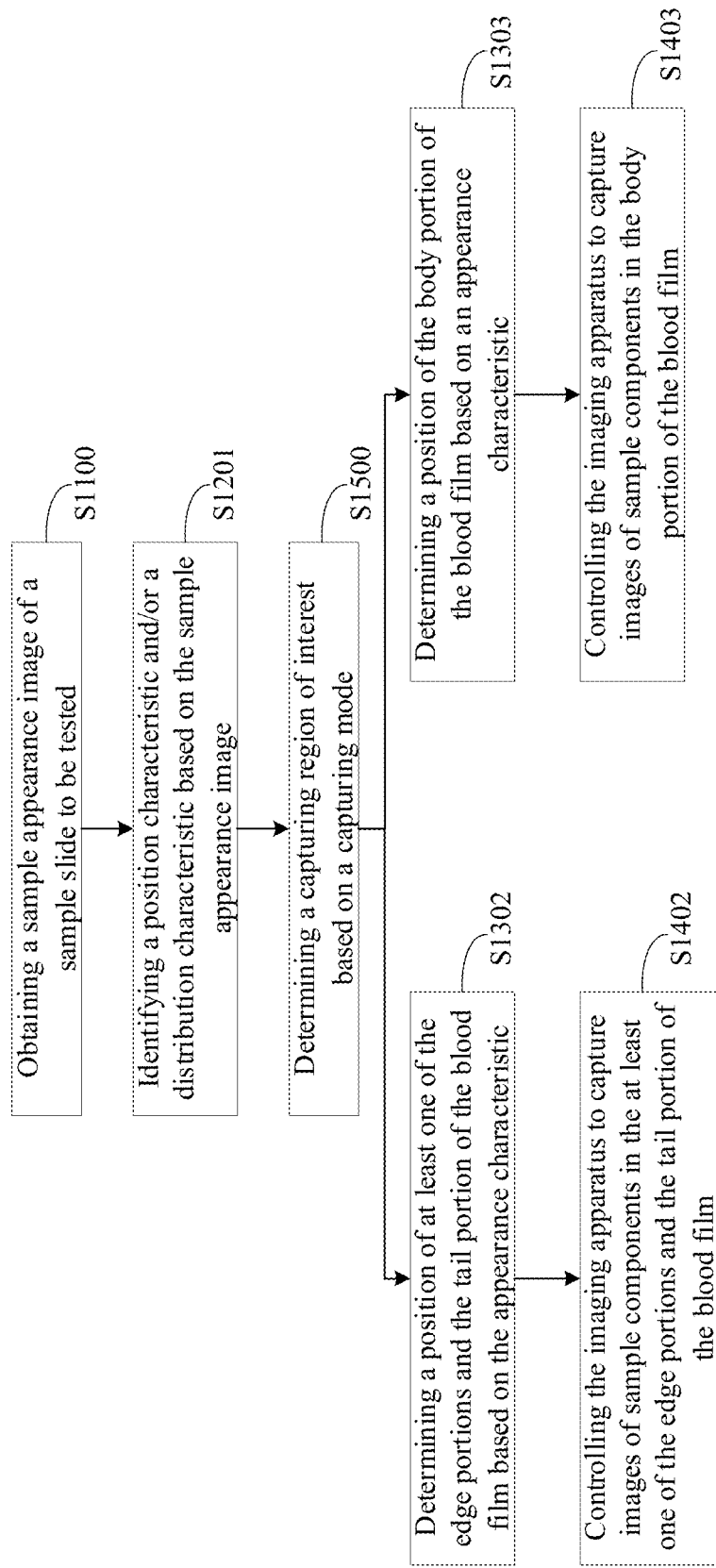
FIG. 15 is a schematic flowchart of a sample image capturing method according to still another embodiment of the disclosure.

In a specific embodiment, the sample slide to be tested is a blood smear smeared with a blood film, and the blood film sequentially includes a head portion, a body portion, and a tail portion on the blood smear in a smearing direction. Herein, as shown in FIG. 15, step S1301 may include step S1302: when the capturing mode is a platelet capturing mode, determining that the capturing region of interest includes an edge portion and/or the tail portion of the blood film based on the platelet capturing mode, and determining a position of the edge portion and/or the tail portion of the blood film on the sample slide to be tested based on the appearance characteristic. Step S1401 may include step S1402: controlling the imaging apparatus to capture, at the determined position, images of sample components in the edge portion and/or the tail portion of the blood film.

Further, as shown in FIG. 15, step S1301 may include step S1303: when the capturing mode is a white-blood-cell capturing mode, determining the body portion of the blood film as the capturing region of interest based on the white-blood-cell capturing mode, and determining a position of the body portion of the blood film on the sample slide to be tested based on the appearance characteristic. Step S1401 may include step S1403: controlling the imaging apparatus to capture, at the determined position, images of sample components in the body portion of the blood film.

Alternatively or additionally, step S1300 includes: determining a capturing path and/or a capturing range of the sample film on the sample slide to be tested based on the appearance characteristic. Step S1400 includes: controlling the imaging apparatus to capture images of the sample film on the sample slide to be tested based on the capturing path and/or capturing range.

For example, for a sample slide prepared from a peripheral blood sample, according to the disclosure, a length, a width, a shape of a tail, etc. of the blood film (blood smear layer) are identified by using the sample appearance image, then a capturing position and a capturing region are determined, especially avoiding abnormal capturing regions such as holes, stripes, and scratches.

For a body fluid sample, according to the disclosure, it can automatically switch to the body fluid mode, and capturing and analysis are performed based on a capturing mode preset by a user. A position of the body fluid smear (sample smear layer or sample film) and a contour boundary (sample capturing range) of the body fluid smear are determined by further analyzing the sample appearance image, and the imaging apparatus and the sample holding apparatus are controlled to move relative to each other based on the determined position and contour boundary, so that the imaging apparatus can capture images of sample components within the sample capturing range at the determined smear layer position.

Alternatively or additionally, step S1300 may include: determining a type of the sample film based on the appearance characteristic. Correspondingly, step S1400 may include: controlling the imaging apparatus to capture, with a capturing parameter corresponding to the type of the sample film, images of sample components in the sample film on the sample slide to be tested.

For other advantages and features of the sample image capturing method 1000, reference may be made to the above description of the sample image capturing system 100 in the disclosure, and details are not described herein again.

The disclosure further provides a computer-readable storage medium having executable instructions stored thereon, and the executable instructions, when executed by a computer, cause the computer to implement the following method steps:

obtaining a sample appearance image of a side of the sample slide to be tested, on which side the sample film to be tested is applied, wherein the sample appearance image includes at least an appearance image of the sample film;

identifying an appearance characteristic of the sample film based on the sample appearance image and determining a capturing parameter based on the appearance characteristic; and instructing an imaging apparatus to capture, with the capturing parameter, images of sample components in the sample film on the sample slide to be tested.

The computer-readable storage medium according to the disclosure is used in particular for implementing the sample image capturing method 1000.

The foregoing computer-readable storage medium may be a volatile memory or a non-volatile memory, or may include both a volatile memory and a non-volatile memory. The non-volatile memory may be a read-only memory, a programmable read-only memory, an erasable programmable read-only memory, an electrically erasable programmable read-only memory, a magnetic random access memory, a flash memory, a magnetic surface memory, an optical disc, or a compact disc read-only memory. The magnetic surface memory may be a magnetic disk memory or a magnetic tape memory. The volatile memory may be a random access memory, and is used as an external cache. By way of example instead of limitation, many forms of RAMs are available, such as a static random access memory, a synchronous static random access memory, a dynamic random access memory, a synchronous dynamic random access memory, a double data rate synchronous dynamic random access memory, an enhanced synchronous dynamic random access memory, a synchlink dynamic random access memory, and a direct rambus dynamic random access memory.

The features or combinations thereof mentioned above in the description, accompanying drawings, and claims can be combined with each other arbitrarily or used separately as long as they are meaningful within the scope of the disclosure and do not contradict each other. The advantages and features described for the sample image capturing system provided in the disclosure are applicable in a corresponding manner to the sample image capturing method and the computer-readable storage medium provided in the disclosure, and vice versa.

The foregoing description merely relates to the preferred embodiments of the disclosure, and is not intended to limit the patent scope of the disclosure. All equivalent variations made by using the content of the specification and the accompanying drawings of the disclosure under the concept of the disclosure, or the direct/indirect applications of the contents in other related technical fields all fall within the scope of patent protection of the disclosure.

What is claimed is:

1. A biological sample image capturing system for a cell morphology analyzer, comprising:
   a biological sample holding apparatus configured to hold a biological sample slide to be tested on which a biological sample film to be tested is applied, wherein the biological sample comprises at least one of a peripheral blood sample, a bone marrow sample, a body fluid sample, and a malaria sample;
   an imaging apparatus configured to capture images of a biological sample on the biological sample slide to be tested that is held by the biological sample holding apparatus;
   a biological sample appearance image obtaining apparatus configured to obtain a biological sample appearance image of a side of the biological sample slide to be tested, on which side the biological sample film to be tested is applied, wherein the biological sample appearance image comprises at least an appearance image of the biological sample film; and
   a controller communicatively connected to the imaging apparatus and the biological sample appearance image obtaining apparatus and configured to: obtain the biological sample appearance image from the biological sample appearance image obtaining apparatus, identify an appearance characteristic of the biological sample film based on the biological sample appearance image, determine a capturing parameter based on the appearance characteristic, and control the imaging apparatus to capture, with the capturing parameter, images of biological sample components in the biological sample film on the biological sample slide to be tested.

2. The biological sample image capturing system of claim 1, wherein the appearance characteristic comprises a position characteristic of the biological sample film on the biological sample slide to be tested; and
the controller is further configured to determine a position of a capturing region of interest of the biological sample film on the biological sample slide to be tested based on the appearance characteristic, and control the imaging apparatus to capture images of biological sample components within the capturing region of interest at the determined position.

3. The biological sample image capturing system of claim 2, wherein the biological sample image capturing system further comprises a mode obtaining apparatus configured to obtain a capturing mode for the biological sample slide to be tested; and
the controller is further communicatively connected to the mode obtaining apparatus and is further configured to: before determining the position of the capturing region of interest, obtain the capturing mode for the biological sample slide to be tested from the mode obtaining apparatus, and determine the capturing region of interest based on the capturing mode.

4. The biological sample image capturing system of claim 3, wherein the biological sample slide to be tested is a blood smear smeared with a blood film, and the blood film sequentially comprises a head portion, a body portion, and a tail portion on the blood smear in a smearing direction and further comprises two edge portions; and
the controller is further configured to: when the capturing mode obtained from the mode obtaining apparatus is a platelet capturing mode, determine that the capturing region of interest comprises at least one of the edge portions and the tail portion of the blood film based on the platelet capturing mode, determine a position of the at least one of the edge portions and the tail portion of the blood film based on the appearance characteristic, and control the imaging apparatus to capture, at the determined position, images of biological sample components in the at least one of the edge portions and the tail portion of the blood film.

5. The biological sample image capturing system of claim 4, wherein the controller is further configured to: when the capturing mode obtained from the mode obtaining apparatus is a white-blood-cell capturing mode, determine the body portion of the blood film as the capturing region of interest based on the white-blood-cell capturing mode, determine a position of the body portion of the blood film based on the appearance characteristic, and control the imaging apparatus to capture, at the determined position, images of biological sample components in the body portion of the blood film.

6. The biological sample image capturing system of claim 3, wherein the biological sample slide to be tested is further provided with a label containing biological sample identity information, and the biological sample identity information is associated with the capturing mode for the biological sample slide to be tested;
the mode obtaining apparatus is further configured to obtain the biological sample identity information of the biological sample slide to be tested from the label of the biological sample slide to be tested; and
the controller is further configured to obtain the capturing mode for the biological sample slide to be tested based on the biological sample identity information obtained from the mode obtaining apparatus.

7. The biological sample image capturing system of claim 6, wherein the controller is further communicatively connected to a hematology analyzer or a central controller, the central controller being communicatively connected to the hematology analyzer, so that the controller is capable of obtaining, based on the biological sample identity information obtained from the mode obtaining apparatus, the capturing mode for the biological sample slide to be tested from the hematology analyzer or the central controller, wherein the capturing mode for the biological sample slide to be tested is obtained by the hematology analyzer by testing a biological sample from same subject as the biological sample on the biological sample slide to be tested, and is stored in the hematology analyzer or the central controller in association with the biological sample identity information of the biological sample slide to be tested.

8. The biological sample image capturing system of claim 1, wherein the appearance characteristic comprises at least one of a position characteristic and a distribution characteristic of the biological sample film on the biological sample slide to be tested; and
the controller is further configured to determine a capturing path and/or a capturing range of the biological sample film on the biological sample slide to be tested based on the appearance characteristic, and control the imaging apparatus to capture images of the biological sample film on the biological sample slide to be tested based on the capturing path and/or capturing range.

9. The biological sample image capturing system of claim 1, wherein the biological sample image capturing system further comprises an oil applying apparatus configured to apply oil on the biological sample slide to be tested that is held by the biological sample holding apparatus, wherein the capturing parameter comprises information about whether to apply oil; and
the controller is further configured to: when it is determined to apply oil on the biological sample slide to be tested based on the appearance characteristic, control the oil applying apparatus to apply oil on the biological sample slide to be tested before controlling the imaging apparatus to perform image capturing.

10. The biological sample image capturing system of claim 1, wherein the controller is further configured to determine a type of the biological sample film based on the appearance characteristic, and determine the capturing parameter based on the type of the biological sample film.

11. The biological sample image capturing system of claim 1, wherein the imaging apparatus comprises a first camera, and the biological sample appearance image obtaining apparatus is configured as a second camera different from the first camera of the imaging apparatus.

12. A biological sample image capturing system for a cell morphology analyzer, comprising:
a biological sample holding apparatus configured to hold a biological sample slide to be tested on which a biological sample film to be tested is applied, wherein the biological sample comprises at least one of a peripheral blood sample, a bone marrow sample, a body fluid sample, and a malaria sample;

an imaging apparatus configured to capture images of a biological sample on the biological sample slide to be tested that is held by the biological sample holding apparatus; and a controller communicatively connected to the imaging apparatus and configured to: receive a capturing parameter corresponding to a biological sample appearance image of the biological sample slide to be tested, and control the imaging apparatus to capture, with the capturing parameter, images of biological sample components on the biological sample slide to be tested, wherein the biological sample appearance image comprises at least an appearance image of the biological sample film.

13. A biological sample image capturing method, comprising:

obtaining, from a biological sample appearance image obtaining apparatus, a biological sample appearance image of a side of a biological sample slide to be tested, on which side a biological sample film to be tested is applied, wherein the biological sample appearance image comprises at least an appearance image of the biological sample film, wherein the biological sample comprises at least one of a peripheral blood sample, a bone marrow sample, a body fluid sample, and a malaria sample;

identifying an appearance characteristic of the biological sample film based on the biological sample appearance image and determining a capturing parameter based on the appearance characteristic; and controlling an imaging apparatus to capture, with the capturing parameter, images of biological sample components in the biological sample film on the biological sample slide to be tested.

14. The biological sample image capturing method of claim 13, wherein:

identifying an appearance characteristic of the biological sample film based on the biological sample appearance image comprises: identifying at least one of a position characteristic and a distribution characteristic of the biological sample film on the biological sample slide to be tested based on the biological sample appearance image;

determining a capturing parameter based on the appearance characteristic comprises: determining a position of a capturing region of interest of the biological sample film on the biological sample slide to be tested based on the appearance characteristic; and controlling an imaging apparatus to capture images comprises: controlling the imaging apparatus to capture images of biological sample components within the capturing region of interest at the determined position.

15. The biological sample image capturing method of claim 14, further comprising:

before determining the position of the capturing region of interest, obtaining a capturing mode for the biological sample slide to be tested from a mode obtaining apparatus, and determining the capturing region of interest based on the capturing mode.

16. The biological sample image capturing method of claim 15, wherein the biological sample slide to be tested is a blood smear smeared with a blood film, and the blood film sequentially comprises a head portion, a body portion, and a tail portion on the blood smear in a smearing direction and further comprises two edge portions; and determining a capturing parameter based on the appearance characteristic comprises: when the capturing mode is a platelet capturing mode, determining that the capturing region of interest comprises at least one of the edge portions and the tail portion based on the platelet capturing mode, and determining a position of the at least one of the edge portions and the tail portion of the blood film based on the appearance characteristic; and controlling the imaging apparatus to capture images of the capturing region of interest comprises: controlling the imaging apparatus to capture, at the determined position, images of biological sample components in the at least one of the edge portions and the tail portion of the blood film.

17. The biological sample image capturing method of claim 16, wherein:

determining a capturing parameter based on the appearance characteristic comprises: when the capturing mode is a white-blood-cell capturing mode, determining the body portion of the blood film as the capturing region of interest based on the white-blood-cell capturing mode, and determining a position of the body portion of the blood film based on the appearance characteristic; and controlling the imaging apparatus to capture images of the capturing region of interest comprises: controlling the imaging apparatus to capture, at the determined position, images of biological sample components in the body portion of the blood film.

18. The biological sample image capturing method of claim 14, wherein the appearance characteristic comprises at least one of a position characteristic and a form distribution characteristic of the biological sample film on the biological sample slide to be tested; and determining a capturing parameter based on the appearance characteristic comprises: determining a capturing path and/or a capturing range of the biological sample film on the biological sample slide to be tested based on the appearance characteristic; and controlling the imaging apparatus to capture images of the capturing region of interest comprises: controlling the imaging apparatus to capture images of the biological sample film on the biological sample slide to be tested based on the capturing path and/or capturing range.

19. The biological sample image capturing method of claim 13, wherein:

determining a capturing parameter based on the appearance characteristic comprises: determining a type of the biological sample film based on the appearance characteristic; and controlling an imaging apparatus to capture the images comprises: controlling the imaging apparatus to capture, with a capturing parameter corresponding to the type of the biological sample film, images of biological sample components in the biological sample film on the sample slide to be tested.

* * * * *